United States Patent [19]

Lokken

[11] Patent Number: 4,778,456
[45] Date of Patent: Oct. 18, 1988

[54] METHOD OF STERILIZING AN OPERATING FIELD AND STERILIZED CASSETTE THEREFOR

[76] Inventor: Oddvin Lokken, 131 Forest Ave., Rye, N.Y. 10580

[21] Appl. No.: 129,527

[22] Filed: Dec. 7, 1987

Related U.S. Application Data

[63] Continuation-in-part of Ser. No. 34,787, Apr. 3, 1987.

[51] Int. Cl.⁴ ............................................ A61M 35/00
[52] U.S. Cl. ..................................... 604/290; 604/25; 604/305
[58] Field of Search ...................... 604/20, 49, 23, 289, 604/305, 905, 290

[56] References Cited

U.S. PATENT DOCUMENTS 3,367,332  2/1968  Groves ............................... 604/290
4,624,656  11/1986  Clark et al. ......................... 604/289

Primary Examiner—Stephen C. Pellegrino
Attorney, Agent, or Firm—Jacobs & Jacobs

[57] ABSTRACT

A sterilized cassette and a transparent cover for the cassette are stored in sterile packaging. A sterilizing gas flows through the cassette to maintain the operating field sterile while the cassette is in place on the patient.

9 Claims, 2 Drawing Sheets

METHOD OF STERILIZING AN OPERATING FIELD AND STERILIZED CASSETTE THEREFOR

The present application is a continuation-in-part of my copending application Ser. No. 034,787, filed Apr. 3, 1987, entitled "Sterile Cassette", which is incorporated herein by reference thereto.

The present invention relates to a method of maintaining a sterilized operating field and a sterilized cassette therefor.

The need to maintain an operating field free from infectious organisms manifests itself in many ways. Surgical incisions may become infected from airborne organisms or from wound exudates Trauma sites, e.g. injuries, burns etc., may become infected in the same way. This is particularly true in the case of long term treatment of a patient by means of introducing nutrients, medication or the like via a catheter or cannula.

The present invention overcomes these problems by providing a sterile cassette having an open top and open bottom The open bottom of the cassette is secured to the dermis to enclose an operating field, after which the operating field is sterilized by UV light and the open top of the cassette is closed by a sterile cover. Thereafter, a sterilizing gas is continuously flowed into the cassette, over the operating field and out of the cassette The operating field is thus at all times kept free of infectious organisms as long as the cassette is in place.

The present invention is illustrated in terms of its preferred embodiments in the accompanying drawings, in which.

Figure 1:
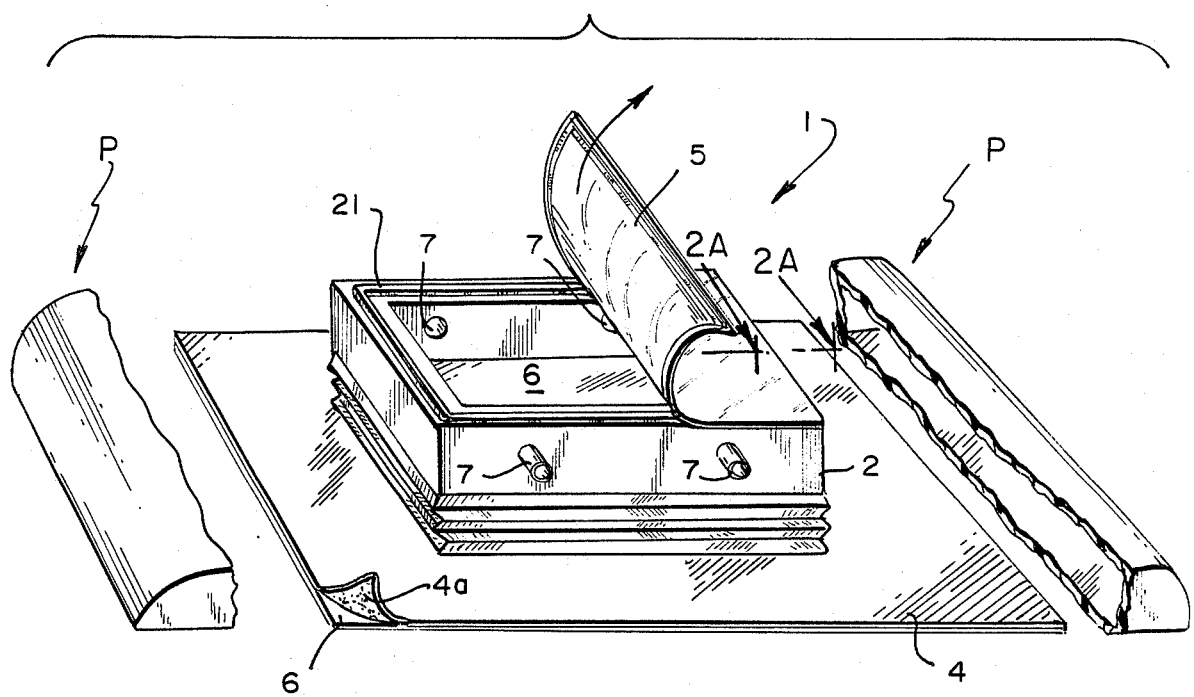
FIG. 1 is a view in perspective of the cassette of the present invention with parts broken away for clarity.

As seen in FIG. 1, cassette 1 of the invention is stored within sterile packaging P and comprises a rigid tubular wall 2 having an open top end and open bottom end, a flexible bellows-like skirt 3 depending from the bottom end of tubular wall 2 and a flexible flange portion 4 extending away from the skirt 3. Protective sheets 5,6 suitably made of paper or plastic, are removably adhesively secured to the top of wall 2 and across the entire underside of flange portion 4 (FIG. 2A), respectively. In particular, sheet 5 carries a pressure-sensitive adhesive (not shown) for removably adhering to wall 2, whereas sheet 6 removably adheres to the pressure-sensitive adhesive 4a (FIG. 1) on the underside of flange portion 4.

Wall 2 is preferably made of rigid plastic so as to withstand handling during use. Skirt 3 is preferably of flexible rubber or plastic and may be pleated as shown so as to conform to the area of the dermis of the patient where the operating field is to be established. Skirt 3 may be secured to wall 2 by adhesive or by heat welding, as desired. Flange 4 is preferably integral with skirt 3, and is also sufficiently flexible to conform to the dermis and create a gas-tight seal around the operating field. Adhesive 4a may be any suitable pressure-sensitive adhesive, such as used in connection with wound dressings.

Figure 3:
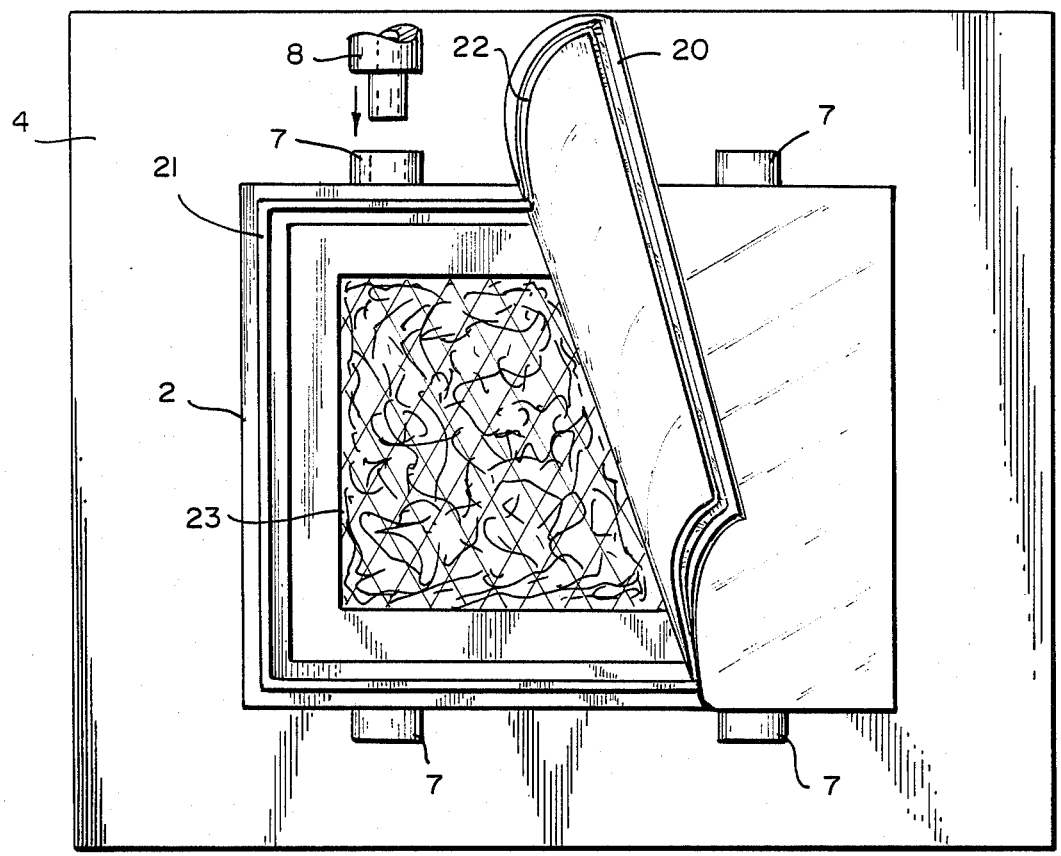
FIG. 3 is a plan view of the cassette of FIG. 1 with the cover being shown folded back only for clarity.
Figure 4:
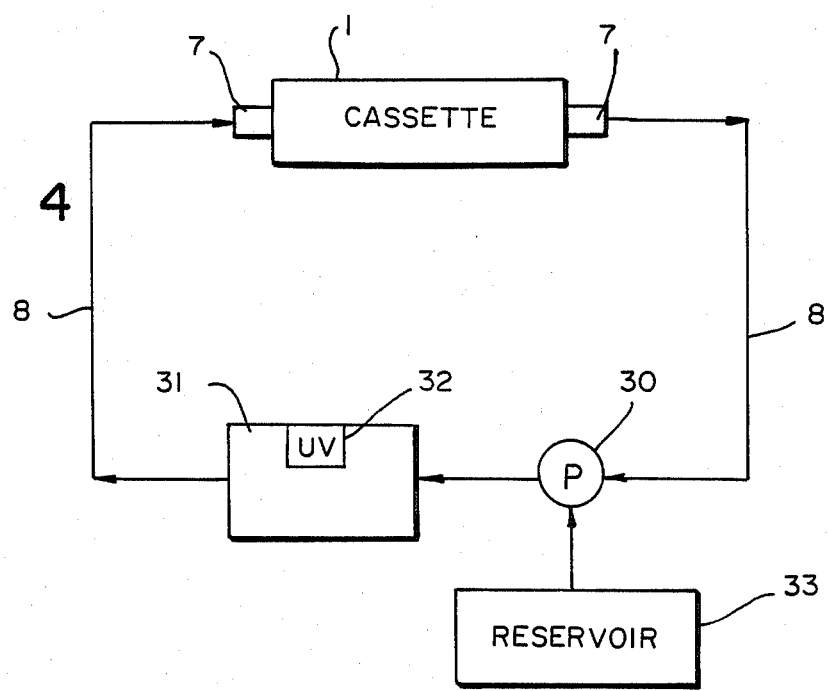
FIG. 4 is a schematic diagram showing the system for flowing sterilizing gas into the cassette.

Ports 7 communicate with the interior of cassette 1 and are provided with suitable means (not shown) for attachment to conduits 8 (FIG. 4), which are used to flow a sterilizing gas into and out of the cassette 1 as will be described below. Such attachment means may be suitable fittings, such as used in connecting IV assemblies together as illustrated in FIG. 3.

Separately stored in its own sterile packaging (not shown) is transparent cover 20 (FIG. 3), which will be described hereinafter. Any suitable transparent plastic may be used for cover 20.

After packaging P is opened, the user removes and discards protective covers 5,6 from cassette 1 and secures the cassette 1 to the dermis by means of adhesive 4a on the underside of flange 4. The operating field within wall 2 is cleansed before or after the cassette 1 is affixed to the dermis and is irradiated through the open top of cassette 1 with ultraviolet light in a manner known per se. This sterilizes the exposed skin within wall 2. Alternatively, the operating field may be irradiated with UV light before the cassette 1 is affixed to the patient.

Figures 2A, 2B:
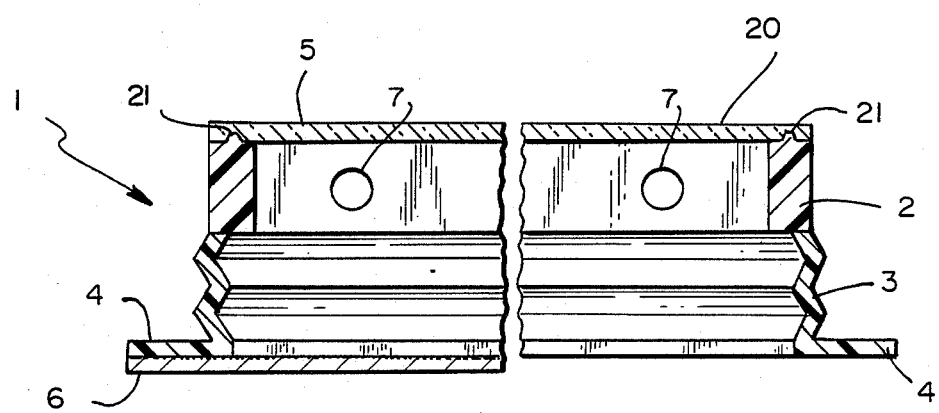
FIG. 2A is a detail view in section taken along lines 2A—2A in FIG. 1.
FIG. 2B is a view similar to FIG. 2A, but with the protective sheets of FIG. 1 removed and the cover in place.

Cover 20 is removed from its sterile packaging (not shown) and is secured to wall 2 by suitable means, such as bead 21 and groove 22 (FIG. 2B). It is noted that FIG. 3 shows cover 20 partially pulled back for clarity only. Once cover 20 is installed, it is intended to remain secured to wall 2 in order to maintain the sterility of the operating field at all times.

With the cassette 1 in place, each conduit 8 (FIG. 4) is attached at one end to a port 7 on either side of cassette 1 and at the other end to pump 30 and chamber 31, respectively. Pump 30 may be any type of medically acceptable pump and is used to pump a sterilizing gas, such as oxygen or ozone, in a closed loop through chamber 31 to cassette 1 and back to chamber 31. Chamber 31 is provided with an ultraviolet lamp 32, such as used with drinking water dispensers, that irradiates the recycled sterilizing gas exhausted from cassette 1 with an effective dose of ultraviolet radiation to sterilize the gas.

Sterilizing gas is thus admitted into the cassette 1 through one port 7 and exhausted from the cassette 1 by the other port 7, thereby contacting the operating field and providing the desired effect of sterilizing the operating field and/or promoting healing. For example, high levels of oxygen are known to promote healing and to prevent growth of anaerobic bacteria. Ozone is known as a sterilizing gas. Hence, oxygen or ozone are suitable gases for use in the present invention.

Sufficient sterilizing gas to start the cycle and to replenish losses is obtained from reservoir 32. Appropriate pressure control equipment (not shown) is preferably used to maintain a pressure slightly above atmospheric, such as about 0.5 to about 5 psig, in order to prevent inflow of airborne organisms into the cassette 1, although it will usually suffice to use a fan or the like as pump 30, whereby the sterilizing gas will be at atmospheric pressure.

FIG. 3 shows a surgical or wound dressing 23 within wall 2 of cassette 1. Suitably, the dressing 23 can be applied to the skin before or after the cassette 1 is secured to the skin, and preferably after the operating field has been irradiated.

When dressing 23 is to be changed, the flow of sterilizing gas is discontinued, after which cover 20 is removed to permit dressing 23 to be removed and replaced, if necessary. The operating field is then irradiated with UV light as described above and a new sterile cover 20 is removed from its sterile packaging (not shown) and secured to cassette 1, whereafter the flow of sterilizing gas is again commenced.

Cassette 1 may be of any convenient size to provide opening 6 with dimensions suitable for use on the human body, such as from about 40 to about 60 mm wide to about 40 to about 90 mm long, depending on the size of the area to be enclosed. The height of wall 2 and bellows 3 may be from about 10 mm to about 30 mm each, or any other convenient size. Preferably, flange 4 extends from about 20 to about 50 mm away from bellows 3. If desired, surgical tape or the like can be placed over flange 4 and onto the patient to provide more secure placement of cassette 1.

Cover 20 is transparent in order to allow viewing of the operating field, and any suitable transparent flexible plastic material may be used as cover 20.

If desired, cassette 1 may be the cassette of my copending application Ser. No. 034,787, filed Apr. 3, 1987, whereby sterilizing gas may be flowed into contact with the operating field therein by connecting conduits 8 of the system of FIG. 4 hereof to appropriate ports of the cassette of my prior application.

It is contemplated that cassette 1 will be provided in a series of sizes, together with templates that define the area enclosed by wall 2. The templates are used to identify the location and size of the pre-operative area of the skin to be prepped so that it will fit within a selected cassette 1. Each template will be provided within its own sterile packaging. Preferably, the templates 40 are conguent to the opening in skirt 3, but they can be a smaller size, if desired.

I claim:
1. A method of maintaining a sterile operating field, which comprises:
    providing first sterile packaging comprising a cassette having tubular wall means open at both ends for enclosing a sterile operating field and means for securing one end of said wall means to the skin of a patient and second sterile packaging comprising a transparent cover means for closing the other end of said cassette;
    removing said sterile cassette and said cover means from said first and second packaging;
    securing said one open end of said cassette via said securing means to a patient to define an operating field within said wall means;
    closing the other open end of said wall means with said cover means; and
    flowing a sterilizing gas into and through said cassette for contact with said operating field on said patient.

2. The method according to claim 1, wherein said sterilizing gas is oxygen or ozone.

3. The method according to claim 1, wherein sterilizing gas is exhausted from said cassette and recycled to said cassette.

4. The method according to claim 3, wherein said exhausted sterilizing gas is irradiated with an effective amount of ultraviolet light to sterilize said exhausted sterilizing gas before it is recycled to said cassette.

5. The method according to claim 1, wherein said operating field is irradiated with an effective dose of ultraviolet light through said open other open end of said cassette after said cassette is secured to said patient, whereafter said other open end is closed by said transparent cover means.

6. The method according to claim 1, wherein the location of said operating field is selected and is irradiated with an effective dose of ultraviolet light, whereafter said cassette is secured to said patient with said irradiated operating field within said wall means.

7. The method according to claim 1, wherein the location of said operating field is selected by applying to the patient a template of a size and shape as to fit within the area enclosed by said wall means, and the area of the skin under said template is identified for subsequent placement of said cassette around said area.

8. The method according to claim 7, wherein said template is congruent to said other open end of said wall means.

9. The method according to claim 7, wherein said template is smaller than said other open end of said wall means.

* * * * *